(12) United States Patent
Chin et al.

(10) Patent No.: US 7,534,243 B1
(45) Date of Patent: May 19, 2009

(54) DISSECTION AND WELDING OF TISSUE

(75) Inventors: Albert K. Chin, Palo Alto, CA (US); Joseph N. Lamberti, Castro Valley, CA (US); Charles J. Adam, San Jose, CA (US); Geoffrey H. Willis, Redwood City, CA (US)

(73) Assignee: Maquet Cardiovascular LLC, San Jose, CA (US)

( * ) Notice: Subject to any disclaimer, the term of this patent is extended or adjusted under 35 U.S.C. 154(b) by 393 days.

(21) Appl. No.: 10/455,942

(22) Filed: Jun. 6, 2003

Related U.S. Application Data

(63) Continuation-in-part of application No. 10/054,477, filed on Jan. 18, 2002, which is a continuation-in-part of application No. 09/413,012, filed on Oct. 5, 1999, which is a continuation of application No. 09/133,136, filed on Aug. 12, 1998.

(51) Int. Cl.
*A61B 18/12* (2006.01)
(52) U.S. Cl. ............................... 606/49; 606/41
(58) Field of Classification Search .............. 606/41–51
See application file for complete search history.

(56) References Cited

U.S. PATENT DOCUMENTS

| | | |
|---|---|---|
| 2,004,559 A | 6/1935 | Wappler et al. |
| 2,028,635 A | 1/1936 | Wappler |
| 2,031,682 A | 2/1936 | Wappler et al. |
| 3,200,028 A | 8/1965 | Chisholm |
| 3,354,478 A | 11/1967 | Allen |
| 3,391,690 A | 7/1968 | Armao |
| 3,439,523 A | 4/1969 | Wood |
| 3,613,682 A | 10/1971 | Naylor |
| 3,625,202 A | 12/1971 | Oyoshirhara et al. |
| 3,772,127 A | 11/1973 | James |
| 3,929,137 A | 12/1975 | Gonser |
| 3,934,115 A | 1/1976 | Peterson |
| 3,938,527 A | 2/1976 | Rioux et al. |
| 4,030,743 A | 6/1977 | Warthen |
| 4,031,898 A | 6/1977 | Hiltebrandt et al. |
| 4,196,734 A | 4/1980 | Harris |
| 4,213,460 A | 7/1980 | Weiner |
| 4,285,753 A | 8/1981 | Warthen |
| 4,315,510 A | 2/1982 | Kihn |
| 4,359,052 A * | 11/1982 | Staub ..................... 606/30 |
| 4,370,980 A | 2/1983 | Lottick |
| 4,493,320 A | 1/1985 | Treat |

(Continued)

FOREIGN PATENT DOCUMENTS

DE  H24669  10/1956

(Continued)

*Primary Examiner*—Henry M Johnson, III
*Assistant Examiner*—Aaron Roane
(74) *Attorney, Agent, or Firm*—Fenwick & West LLP

(57) ABSTRACT

A tissue dissector and method for welding and severing blood vessels includes advancing the tip of a tissue-dissecting surgical instrument through tissue, with a tissue welder substantially concealed within the tip during tissue dissection. Blood vessels encountered in the tissue being dissected are selectively captivated and compressed in substantial contact with the tissue welder to elevate the temperature of the compressed tissue sufficiently to hemostatically weld and sever the compressed blood vessel.

9 Claims, 10 Drawing Sheets

U.S. PATENT DOCUMENTS

| | | |
|---|---|---|
| 4,516,574 A | 5/1985 | Hewes, Jr. |
| 4,597,379 A | 7/1986 | Kihn et al. |
| 4,655,216 A | 4/1987 | Tischer |
| 4,662,068 A | 5/1987 | Polonsky |
| 4,671,274 A | 6/1987 | Sorochenko |
| 4,705,041 A | 11/1987 | Kim |
| 4,979,771 A | 12/1990 | Childs |
| 4,985,030 A | 1/1991 | Melzer et al. |
| 5,046,251 A | 9/1991 | Scott |
| 5,122,137 A | 6/1992 | Lennox |
| 5,147,356 A | 9/1992 | Bhatta |
| 5,151,102 A | 9/1992 | Kamiyama et al. |
| 5,171,255 A | 12/1992 | Rydell |
| 5,190,541 A | 3/1993 | Abele et al. |
| 5,192,280 A | 3/1993 | Parins |
| 5,197,649 A | 3/1993 | Bessler et al. |
| 5,207,691 A | 5/1993 | Nardella |
| 5,217,458 A | 6/1993 | Parins |
| 5,226,890 A | 7/1993 | Ianniruberto et al. |
| 5,226,908 A | 7/1993 | Yoon |
| 5,250,046 A | 10/1993 | Lee |
| 5,258,006 A | 11/1993 | Rydell et al. |
| 5,267,998 A | 12/1993 | Hagen |
| 5,276,306 A | 1/1994 | Huffman |
| 5,290,286 A | 3/1994 | Parins |
| 5,336,221 A | 8/1994 | Anderson |
| 5,336,229 A | 8/1994 | Noda |
| 5,352,222 A | 10/1994 | Rydell |
| 5,360,428 A | 11/1994 | Hutchinson, Jr. |
| 5,376,087 A | 12/1994 | Haber et al. |
| 5,389,098 A | 2/1995 | Tsuruta et al. |
| 5,401,273 A | 3/1995 | Shippert |
| 5,403,312 A | 4/1995 | Yates et al. |
| 5,411,508 A | 5/1995 | Bessler et al. |
| 5,443,463 A | 8/1995 | Stern et al. |
| 5,445,638 A | 8/1995 | Rydell et al. |
| 5,451,223 A | 9/1995 | Ben-Simhon |
| 5,452,513 A | 9/1995 | Zinnbauer et al. |
| 5,458,598 A | 10/1995 | Feinberg et al. |
| 5,480,409 A | 1/1996 | Riza |
| 5,496,317 A | 3/1996 | Goble et al. |
| 5,512,721 A | 4/1996 | Young et al. |
| 5,527,331 A | 6/1996 | Kresch et al. |
| 5,556,563 A | 9/1996 | von der Heyde et al. |
| 5,565,122 A | 10/1996 | Zinnbauer et al. |
| 5,582,611 A | 12/1996 | Tsuruta et al. |
| 5,595,565 A | 1/1997 | Treat et al. |
| 5,601,601 A | 2/1997 | Tal et al. |
| 5,603,698 A | 2/1997 | Roberts et al. |
| 5,647,871 A | 7/1997 | Levine et al. |
| 5,665,085 A | 9/1997 | Nardella |
| 5,688,270 A | 11/1997 | Yates et al. |
| 5,690,847 A | 11/1997 | LaValley et al. |
| 5,693,051 A | 12/1997 | Schulze et al. |
| 5,709,680 A | 1/1998 | Yates et al. |
| 5,730,756 A | 3/1998 | Kieturakis et al. |
| 5,735,848 A | 4/1998 | Yates et al. |
| 5,755,717 A | 5/1998 | Yates et al. |
| 5,776,112 A | 7/1998 | Stephens et al. |
| 5,797,907 A | 8/1998 | Clement |
| 5,807,393 A | 9/1998 | Williamson et al. |
| 5,810,811 A | 9/1998 | Yates et al. |
| 5,817,061 A | 10/1998 | Goodwin et al. |
| 5,827,279 A | 10/1998 | Hughett et al. |
| 5,827,281 A | 10/1998 | Levin |
| 5,843,017 A | 12/1998 | Yoon |
| 5,868,785 A | 2/1999 | Tal et al. |
| 5,871,498 A | 2/1999 | Jervis et al. |
| 5,914,062 A | 6/1999 | von der Heyde |
| 5,976,130 A | 11/1999 | McBrayer et al. |
| 6,077,277 A | 6/2000 | Mollenauer et al. |
| H1904 H | 10/2000 | Yates et al. |
| 6,287,304 B1 * | 9/2001 | Eggers et al. .................. 606/37 |
| 6,432,115 B1 | 8/2002 | Mollenauer et al. |
| 6,544,260 B1 * | 4/2003 | Markel et al. .................. 606/41 |
| 2004/0102804 A1 | 5/2004 | Chin |

FOREIGN PATENT DOCUMENTS

| | | |
|---|---|---|
| DE | 2550693 | 5/1977 |
| DE | 3002088 | 7/1981 |
| DE | 40469 | 8/1987 |
| EP | 0517244 A1 | 12/1992 |
| EP | 0517244 B1 | 12/1992 |
| EP | 0518230 | 12/1992 |
| SU | 639545 | 12/1978 |
| SU | 1498474 | 8/1989 |
| WO | WO 93/08754 | 5/1993 |
| WO | WO 94/24949 | 11/1994 |
| WO | WO 94/24951 | 11/1994 |
| WO | WO 98/38935 | 9/1998 |

* cited by examiner

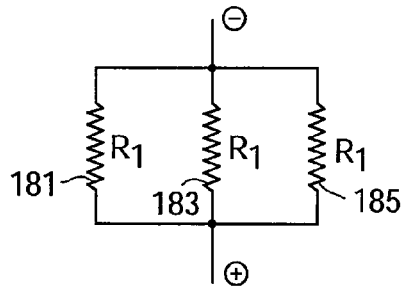
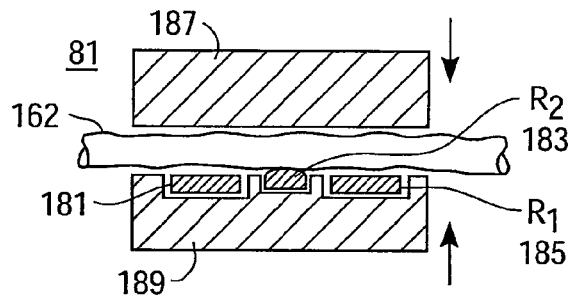
FIG. 21b
FIG. 21a
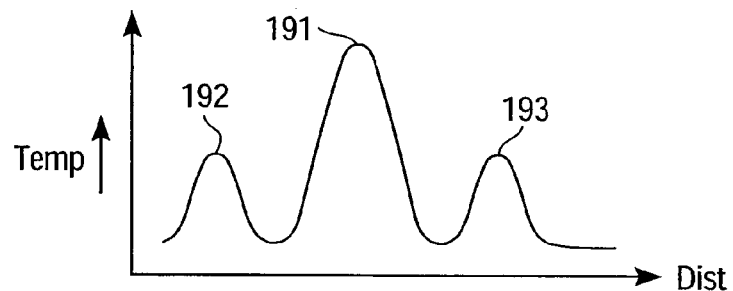
FIG. 21c
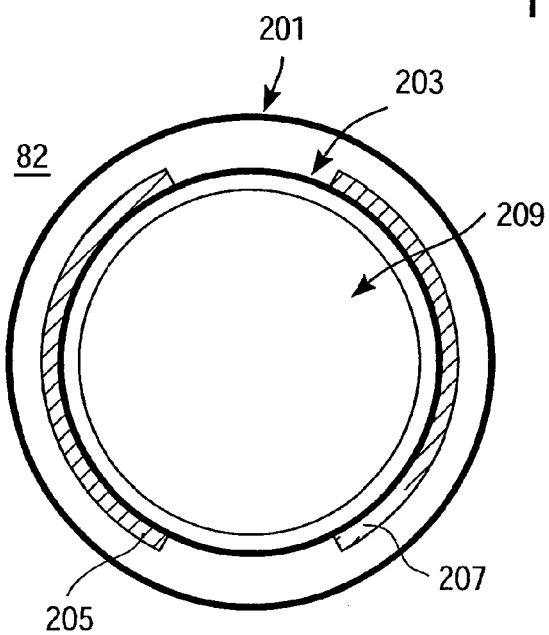
FIG. 22
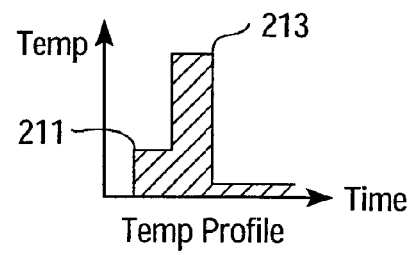
FIG. 23a
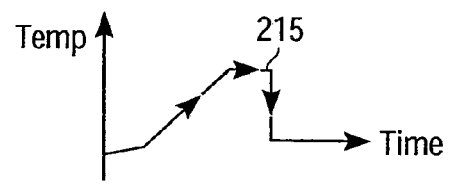
FIG. 23b
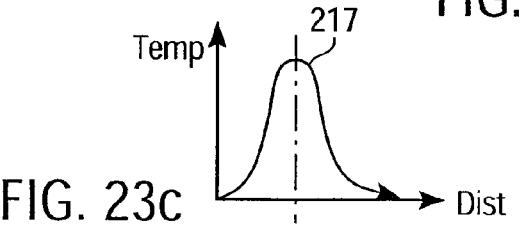
FIG. 23c

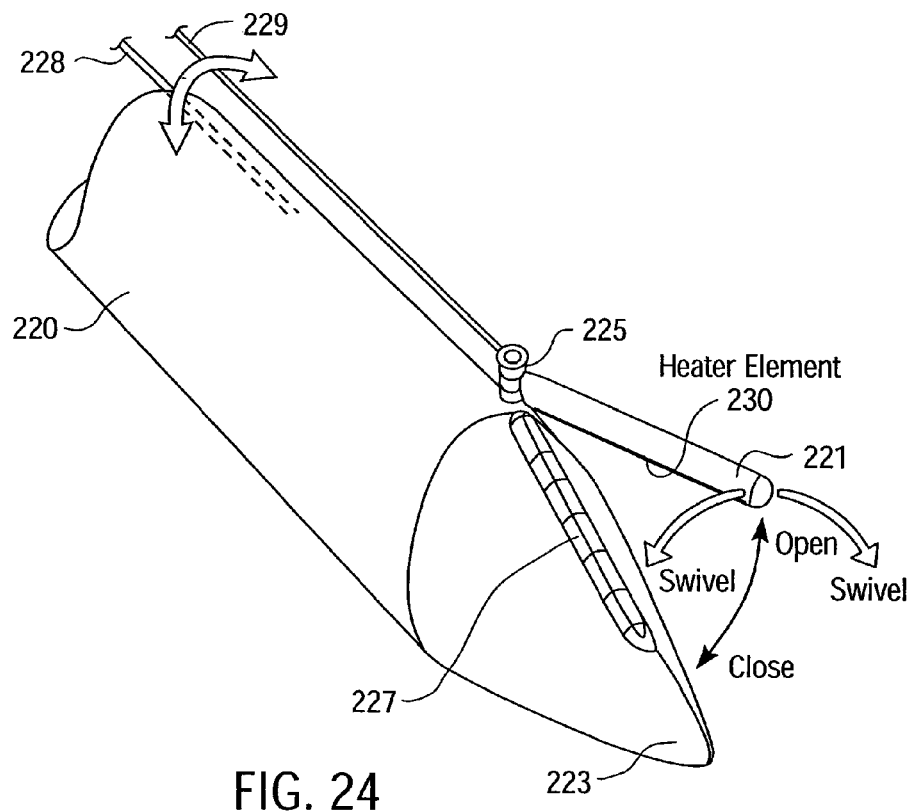
FIG. 24
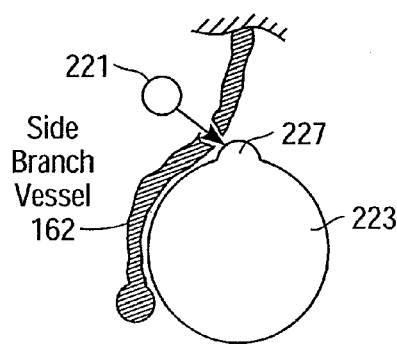 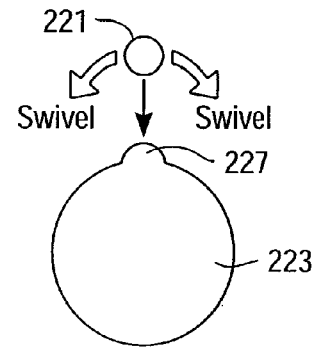 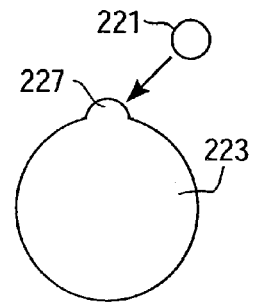
FIG. 25a     FIG. 25b     FIG. 25c

DISSECTION AND WELDING OF TISSUE

RELATED APPLICATIONS

This application is a continuation-in-part of application Ser. No. 10/054,477 entitled "Vessel Harvesting Apparatus and Method", filed on Jan. 18, 2002 by Michael Stewart et al., which is a continuation-in-part of application Ser. No. 09/413,012 entitled "Tissue Dissector Apparatus and Method", filed on Oct. 5, 1999 by Albert K. Chin, which is a continuation of application Ser. No. 09/133,136 entitled "Tissue Dissector Apparatus and Method", filed on Aug. 12, 1998 by Albert K. Chin, which subject matter is incorporated herein by this reference to form a part hereof.

BACKGROUND OF THE INVENTION

Contemporary surgical procedures for harvesting a saphenous vein to be used as a graft vessel in coronary vascular surgery commonly requires a multiple number of surgical instruments first to dissect adjacent tissue to create an anatomical work space about the saphenous vein, and then to ligate and transect lateral vessels away from the saphenous vein. Such procedures use different instruments that are successively inserted and removed as the remote surgical site progresses along the segment of vein being harvested. Such surgical activity is time-consuming, and has a propensity to inflict additional trauma associated, for example, with undesirable avulsion of lateral or side-branch vessels and injury to the target vessel. In addition, conventional RF monopolar and bipolar technologies used to ligate the side branches commonly produce unreliable seals of the vessel side branches that are incapable of withstanding arterial pressures when the vessel is subsequently used as a coronary artery bypass graft, so the side branches of the vessel must also be clipped or sutured prior to use of the vessel as a bypass graft.

SUMMARY OF THE INVENTION

In accordance with one embodiment of the present invention, a tissue welding and transecting instrument as one form of end effector includes a tapered tissue-dissecting tip disposed at a distal end of an elongated cannula and includes an arm that is deployable from substantially flush orientation in the tapered walls of the tissue-dissecting tip to expose tissue structures such as blood vessels to a heater element as a thermal tissue welder. The arm is selectively deployable and the heater-element welder is selectively energized via a foot-pedal control, or via controls disposed on a handle that is attached to a proximal end of the elongated cannula. A tissue structure thus captivated between the arm and wall of the tissue-dissecting tip is compressed and selectively welded and hemostatically severed. The heater element may be recessed into the wall of the tissue-dissecting tip beneath the deployable arm, or may be mounted beneath the arm, or may be otherwise selectively deployable for compressing and welding or cauterizing tissue structures such as blood vessels. In this way, the exterior wall of the tissue-dissecting tip may be configured initially as substantially smooth and devoid of surface protrusions that might undesirably avulse a blood vessel during dissection of tissue in contact with the wall of the tip. As desired, the recessed arm is selectively deployed to clamp a blood vessel and maintain the vessel in contact with the heater element under the arm. The heater element is selectively elevated in temperature, for example, by conduction therethrough of electrical current in one embodiment, or by application thereto of intense radiant-energy flux via a fiber-optical channel in another embodiment to heat the element to sufficiently high temperature to thermally weld the vessel and hemostatically sever the vessel where clamped by the arm into contact with the heater element. Various forms of deployable end effectors and associated electrical heater elements include configurations for selectively compressing and heating a target vessel to weld, seal and sever the vessel.

In another embodiment of the present invention, a tissue-dissecting tip that is disposed at the distal end of an elongated cannula includes an elevated ridge or protrusion on the tissue-engaging outer surface of the tip in substantial alignment with the elongated axis of the cannula. Such ridge or protrusion facilitates concentrating compression force on a tissue structure that is confined against the protrusion during application of heat to form an adequate tissue weld.

BRIEF DESCRIPTION OF THE DRAWINGS

FIG. 10b is a partial side pictorial view of an end effector in the embodiment of FIG. 10a;

FIG. 20b is a partial end sectional view of another embodiment of the end effector for the embodiment of FIG. 20a;

FIG. 21a is a partial end sectional view of another embodiment of an end effector for the embodiment of FIG. 8;

FIG. 21b is a simple schematic representation of the electrical heater elements in the embodiment of FIG. 21a;

FIG. 21c is a graph illustrating a temperature profile achieved across the width of the embodiment of FIG. 21a;

FIG. 22 is an end sectional view of an electrical structure for operating an end effector of the present invention;

FIG. 23a is a graph showing a temperature profile with time of a heater element according to the present invention;

FIG. 23b is a graph showing a profile of elevated temperatures to which a tissue structure is exposed in accordance with one method embodiment of the present invention;

FIG. 23c is a graph showing a profile of elevated temperatures established by an end effector according to the present invention;

FIG. 24 is a partial perspective view of another embodiment of the present invention in which a prong is pivotally mounted for rotation over the tissue-contacting outer surface of a tissue-dissecting tip; and FIGS. 25a, b, c are, respectively, partial end views of the embodiment of FIG. 24 in various operational configurations.

DETAILED DESCRIPTION OF THE INVENTION

Figure 1:
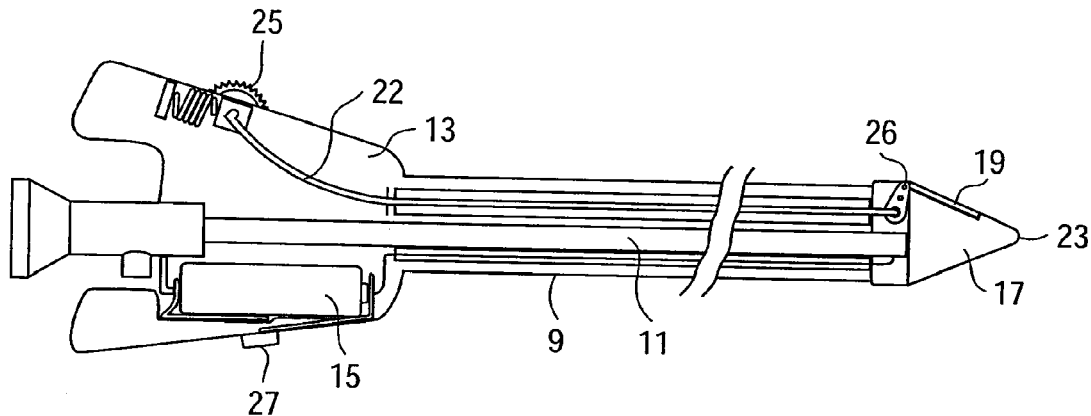
FIG. 1 is a pictorial side view of the surgical instrument in accordance with an embodiment of the invention.
Figure 2:
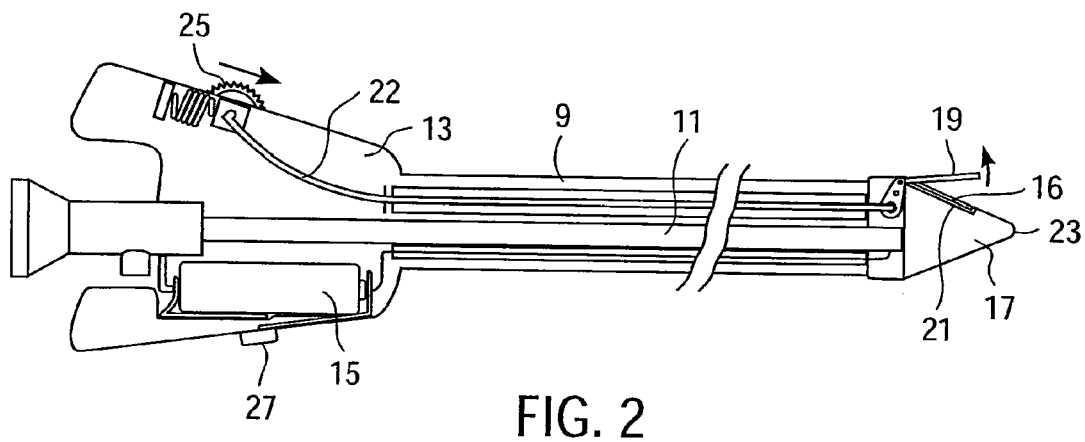
FIG. 2 is a pictorial side view of the surgical instrument of FIG. 1 in an operative configuration.

Referring now to FIGS. 1 and 2, there are shown operational configurations of one embodiment of a surgical instrument in accordance with the present invention including an elongated cannula 9 enclosing an endoscope 11 therein that extends between distal and proximal ends of the cannula. A housing 13 is attached to the proximal end of the cannula 9 to support manual controls, as later described herein, and to enclose a battery 15 source of electrical current in one embodiment for selectively heating a hot-wire tissue welder 16 in the distal tip 17. In another embodiment, a fiber optical channel conveys an intense level of radiant energy, for example, from an external laser to an absorptive load that is thereby heated to tissue-welding temperatures. Alternatively, a source of ultrasonic signal may be connected to an ultrasonic vibrator at the distal tip 17 for selectively ultrasonically welding tissue in contact with the tip 17. 'Welding' of tissue as used herein means fusion of previously separated tissue surfaces sufficient to seal a blood vessel against leakage of blood under pressure.

The tissue-dissecting tip 17 attached to the distal end of the cannula 9 includes conically-tapered exterior and interior transparent walls to facilitate endoscopic visualization through the tip 17 of the dissection of tissue that contacts the exterior walls of the tip 17. An arm 19 is pivotally mounted within a recess 21 in the tapered wall of the tip 17, substantially aligned toward the distal apex 23 of the tip, to swing laterally outwardly from the tapered wall of the tip in response to translational motion of an actuator rod 22 that is linked eccentrically with respect to a pivotal mounting for the arm 19. The actuator rod 22 extends through a lumen in the cannula 9 from the arm 19 near the distal end of the cannula 9 to a control button 25 that is slidably mounted in the housing which is attached to the proximal end of the cannula 9. In this embodiment, sliding the control button 25 distally forward elevates the arm 19 about its pivotal mounting to expose the heater-element tissue welder 16 beneath arm 19. Specifically, such tissue welder in one embodiment includes a length of high resistance wire 16 that can be heated to elevated temperatures of about 2000° F. by conducting electrical current supplied by battery 15. Manually controllable switch 27 for controlling the heating of the wire 16 is provided on the housing 13 at a location that is conveniently operable by the user's thumb or finger. Of course, electrical current can also be supplied from an external source through a foot-operated controller to selectively heat the wire 16. In another embodiment, an intense level of radiant energy is supplied along a fiber optical channel, for example, from an external laser to an absorptive load that is thereby heated to tissue-welding temperature. Alternatively, an ultrasonic crystal resonator or other vibrator may be mounted beneath the arm 19 to ultrasonically heat tissue compressed beneath arm 19 in response to ultrasonic signal applied thereto under control of switch 27.

The arm 19 and heater-element tissue welder 16 may be housed within a shallow recess 21 in the exterior tapered wall of the tip 17 near the base of the conical tip, aligned generally toward the distal apex 23 of the tip. Such shallow recess may be narrow to avoid significantly obstructing the visual field of the endoscope, and is formed of materials that are capable of withstanding the elevated operating temperatures of the heater element 16 that is supported within the recess. In one embodiment, a recessed slot 21 in the conical surface of the tip 17 is sputter-coated with a refractory metal such as platinum to promote heat resistance of the surrounding material such as glass or polycarbonate material that forms the transparent tip 17. The slot ends in an aperture 31 near the base of the conical section of the tip 17, as shown in FIG. 4, through which the arm 19 extends from a lateral pivot axis 26. A flexible boot 29, as shown in FIGS. 3a, b, is sealed to the surface of the tip 17 and to the arm 19 to inhibit entry of tissue and debris into the interior of the tip 17 through the aperture during tissue dissection, and to facilitate movement of the arm 19 into open or capture position, as shown in FIGS. 1 and 2, respectively.

Figure 6A:
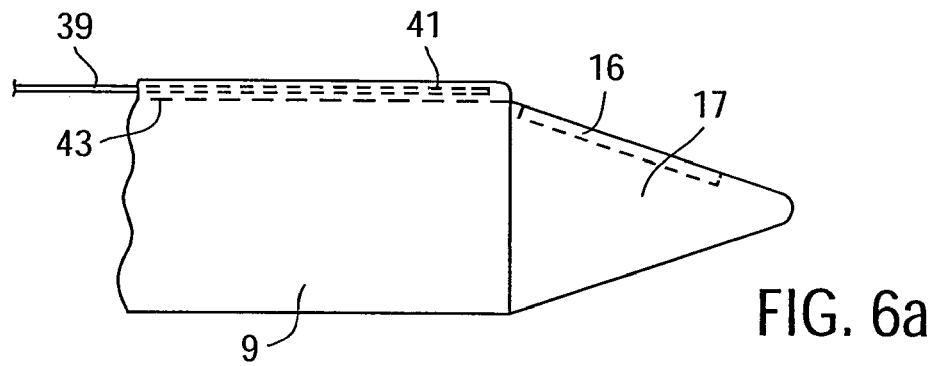
FIGS. 6 a, b, c, d are partial pictorial side views of another embodiment of the surgical instrument of the present invention illustrating operational configurations of the surgical instrument.
Figure 6B:
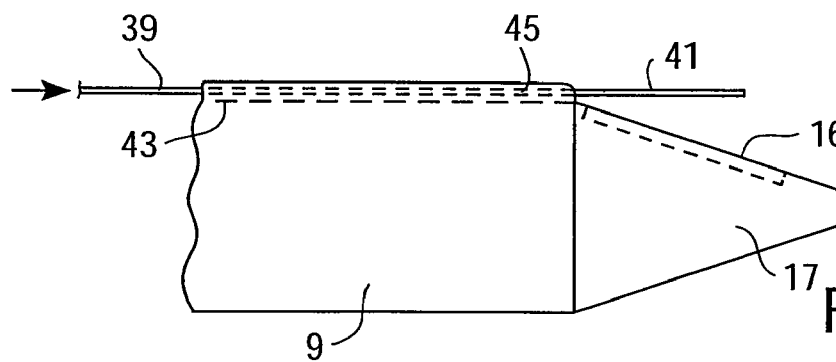
Figure 6C:
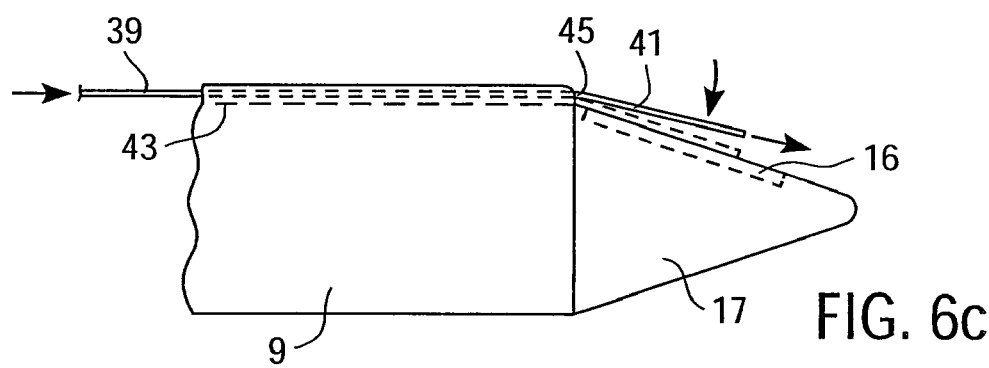
Figure 6D:
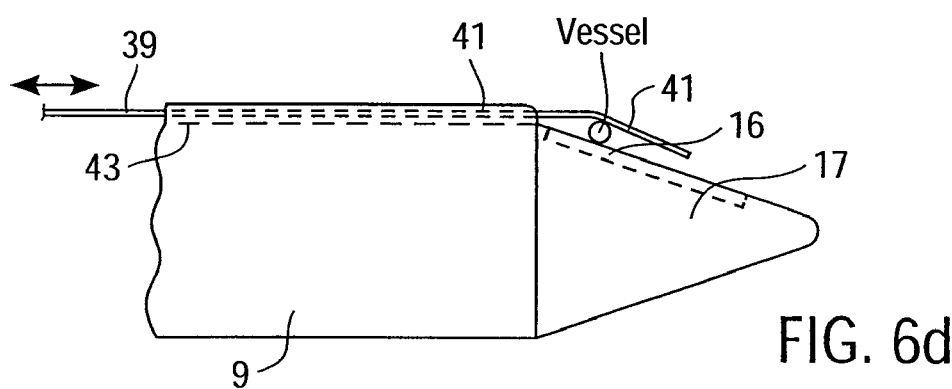

In another embodiment of the present invention, as illustrated in the pictorial side views of FIGS. 6a, b, c, d, a resilient mounting rod 39 supports and spring-biases an arm 41 into a 'closed' configuration, as illustrated in FIG. 6c. When not so fully deployed, the mounting rod 39 retracts the arm 41 into a constraining lumen 43 within the cannula 9, as illustrated in FIG. 6a. A resilient bend 45 in the mounting rod 39 is straightened as retracted into the constraining lumen 43 to configure the arm 41 in an 'open' or capture mode, as illustrated in FIG. 6b. The maximally-extended position of the rod 39, as shown on FIG. 6d, configures the end effector for capturing a side-branch vessel and maneuvering the vessel into contact with the heater element tissue welder 16.

Figure 3A:
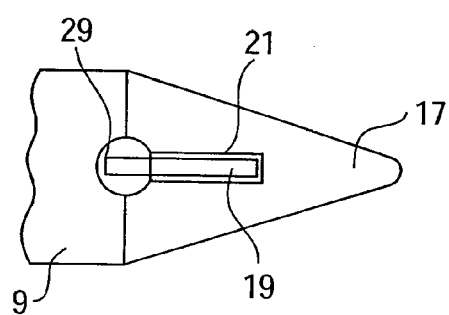
FIGS. 3 a, b are, respectively, partial top and side views of the distal tip of the surgical instrument of FIG. 1 showing the configuration of the deployable arm.
Figure 3B:
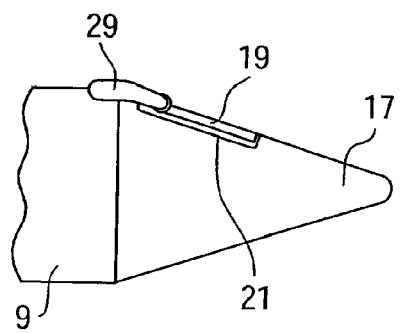
Figure 4:
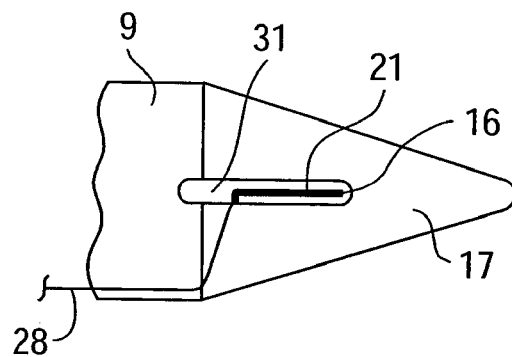
FIG. 4 is a partial top view of the distal tip of the surgical instrument of FIG. 1 with the deployable arm omitted.

In operation, the arm 19, 41 is retained in retracted or closed position, as shown in FIGS. 1 and 3 a, b, 6a during the dissection of tissue to form an anatomical space, for example, along the saphenous vein during surgical procedures to harvest the vessel from the body. In the closed configuration of the embodiment of FIGS. 1, 3a, 3b, the arm 19 is substantially flush with the outer conical wall of the tissue-dissecting tip 17, and therefore introduces negligible obstruction to the tissue-dissecting procedure and only nominal optical obstruction of the endoscopic visualization through the transparent tip 17. In the retracted configuration of the embodiment of FIG. 6a, the arm 41 resides in the constraining-lumen, and therefore introduces negligible obstruction to the tissue-dissecting procedure performed by tapered tip 17.

Figure 5A:
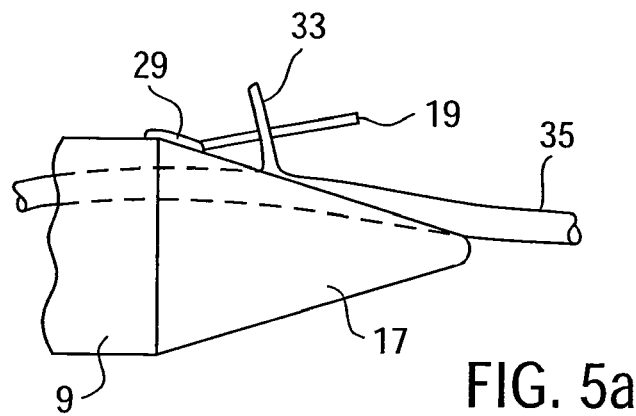
FIGS. 5 a, b, c are partial pictorial side views of the distal tip of the surgical instrument of FIG. 1 showing a sequence of configurations during a surgical procedure.
Figure 5B:
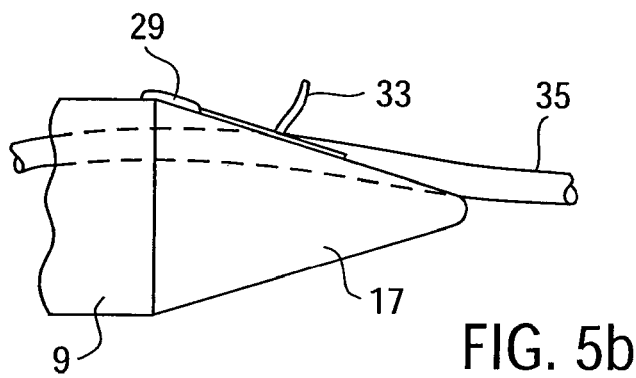
Figure 5C:
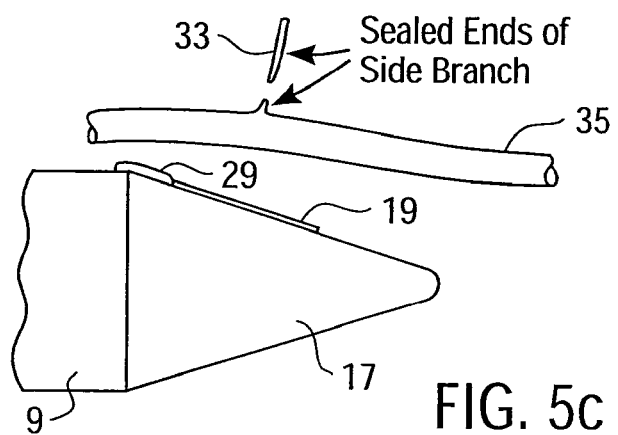

As tissue dissection proceeds along the course of a saphenous vein using the illustrated embodiments of the present invention, any side-branch or tributary vessels encountered along the course may be welded and severed in the manner as shown in FIGS. 5, a, b, c. Specifically, the arm 19 of the instrument of FIG. 1 is pivoted to the open position, and the assembly of cannula 9 and tip 17 and extended arm 19 is maneuvered to 'capture' the side-branch vessel 33 between the arm 19 in open position and the outer wall of the tip 17. The arm 19 is then pivoted to the closed position, as shown in FIG. 5b, to constrain and compress the side-branch vessel 33 under the arm 19 into close proximity to, or direct contact with, the heater-element tissue welder 16 within the recess under the arm 19. The switch 27 is manually closed, and in one embodiment, current supplied to the high-resistance wire 16 from battery 27 heats the wire. In another embodiment, the switch 27 may be connected to control an external laser that supplies intense levels of radiant energy along an optical channel 28 instead of current-carrying wires to an optical absorptive load that is thereby heated to elevated temperatures. Alternatively, ultrasonic signal may be supplied to an ultrasonic resonator or vibrator under arm 19 in response to manual actuation of switch 27. This exposure hemostatically welds and severs the side-branch vessel 33 from the saphenous vein 35 as shown in FIG. 5c, and configures the tip 17 and arm 19 for continued dissection of tissue along the course of the saphenous vein 35 without requiring additional steps to withdraw, reconfigure and replace the instrument.

In the instrument of FIG. 6a, the arm 41 is retracted into the constraining lumen 43 in cannula 9 during blunt tissue dissection by the tapered tip 17. As desired, the mounting rod 39 is extended distally to deploy the arm 41 into the 'open' or capture configuration illustrated in FIG. 6b. Upon further extension of the mounting rod 39 to position the resilient bend 45 distally of the constraining lumen 41, the arm 41 descends toward the tapered wall of the tip into 'closed' configuration, as illustrated in FIG. 6c, to compress a side branch vessel 40 against the heater-element tissue welder 16.

Of course, the heater-element tissue welder 16 may also be mounted on the arm 19, 41 to engage a blood vessel positioned between the arm and the adjacent exterior wall of the tip 17 to conveniently effect hemostatic tissue welding and severing of a lateral vessel so positioned.

The distance from the saphenous vein 35 at which a side branch 33 is severed is conveniently controlled and visually gauged by aligning a side portion of the conical wall of the tapered tip 17 in contact with the saphenous vein 35 and by positioning the side branch vessel 33 at a location along the upper portion of the conical taper at which the arm 19, 41, deployable in a substantially vertical plane, 'captures' the side branch vessel 33, as shown in FIGS. 4, 5a, 5b.

Figure 7:
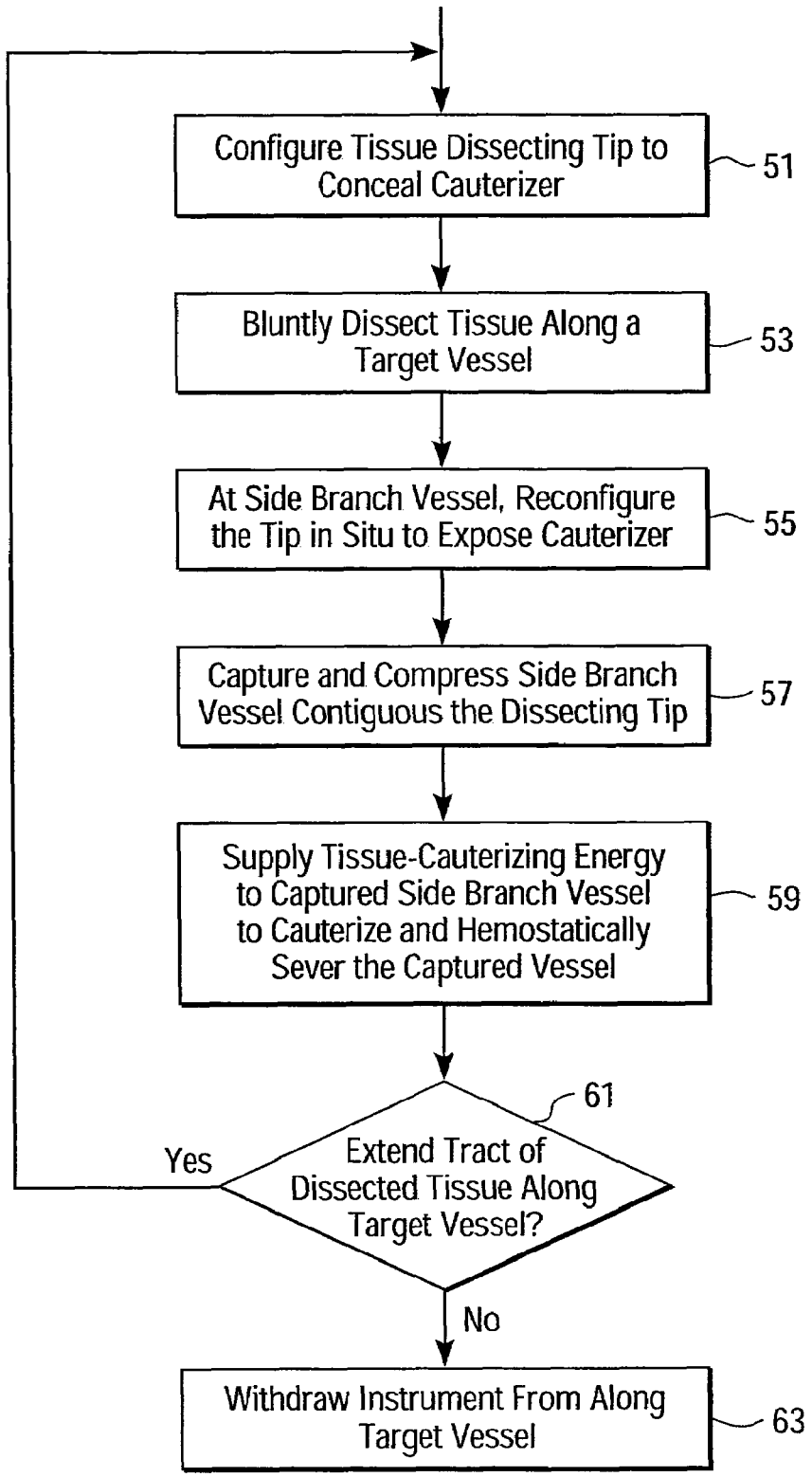
FIG. 7 is a flow chart illustrating the surgical procedure according to one method embodiment of the present invention.

Referring now to the flow chart of FIG. 7, an initial incision is made in conventional manner to expose the target vessel (e.g., the saphenous vein). The dissecting and tissue welding instrument as previously described herein is initially configured 51 in the 'closed' configuration, as previously described herein, to conceal the tissue welder and to provide a substantially unobstructed tapered tip that dissects tissue 53 along the course of the target vessel as the tip is advanced through the adjacent tissue. Such connective tissue may be dissected away from and around one or more side-branch vessels that extend from the target vessel at locations along the course of the vessel. The instrument is then configured 55 in situ within the anatomical space formed in the dissected tissue in order to expose the tissue welder. The controllable arm of the instrument is positioned in the 'open' configuration, as previously described herein, to facilitate capturing the side branch vessel between the arm and the adjacent surface of the tissue-dissecting tapered tip. The arm is then controlled to pinch or compress 57 the side-branch vessel as tissue-welding energy is supplied 59 by the tissue welder to the compressed tissue. The elevated operating temperature of the tissue welder to which the compressed tissue is exposed thus seals the side-branch vessel and hemostatically severs the side-branch vessel substantially at the location where compressed. The instrument may then again be configured in the 'closed' configuration for continuing dissection of tissue in order to extend 61 the anatomical space formed along the target vessel, or for removing the instrument 63 from along the course of the target vessel.

Figure 8:
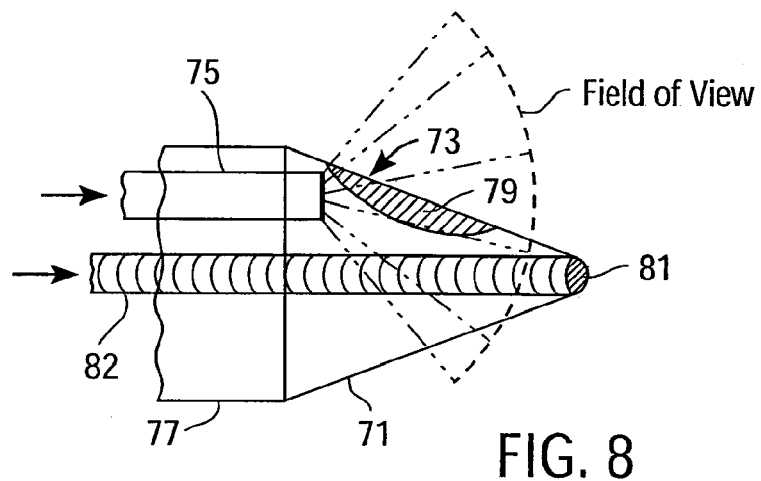
FIG. 8 is partial side sectional view of an embodiment of a tissue dissecting tip according to one embodiment of the invention.
Figure 9:
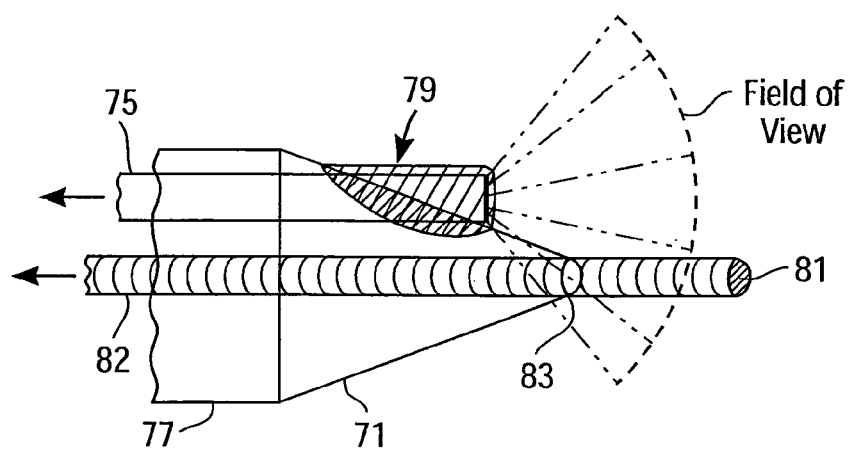
FIG. 9 is a partial side sectional view of the embodiment of FIG. 8 as reconfigured for operation.

Referring now to FIGS. 8 and 9 there are shown partial side sectional views of operational configurations of a dissecting tip in accordance with another embodiment of the present invention in which an endoscope is eccentrically disposed relative to the substantially right conical, rigid tissue-dissecting tip 71. The tip includes a small portion 73 of the conical surface that is flexible at a location axially aligned with the elongated axis of an endoscope 75 which is eccentrically received in and supported by the outer cannula 77. Specifically, the portion 73 of the conical surface may include an aperture in the rigid tip 71 that is covered by an elastic membrane 79 to preserve a seal at the distal end of cannula 77 against bodily fluids and tissue debris, and to facilitate forward positioning of the endoscope through the aperture, as illustrated in FIG. 9. Such repositioning of the endoscope 75 greatly enhances the utility of the assembled cannula 77 for dissecting tissue, for example, along the saphenous vein under visualization through the membrane 79 and the endoscope 75. Extending the endoscope 75 forward through the aperture, as illustrated in FIG. 9, extends the visual field to include an extended end effector 81 which can be selectively extended substantially through and forward of the apex of the conical surface of tip 71. Thus, the field of view of the endoscope 75 may be selectively altered to accommodate use of the assembled cannula 77 and tip 71, as shown in FIG. 8, for dissecting tissue under visualization and, as shown in FIG. 9, for positioning and operating an end effector 81 forward of the dissecting tip 71 under visualization through the endoscope 75 and transparent membrane 79.

Figure 10A:
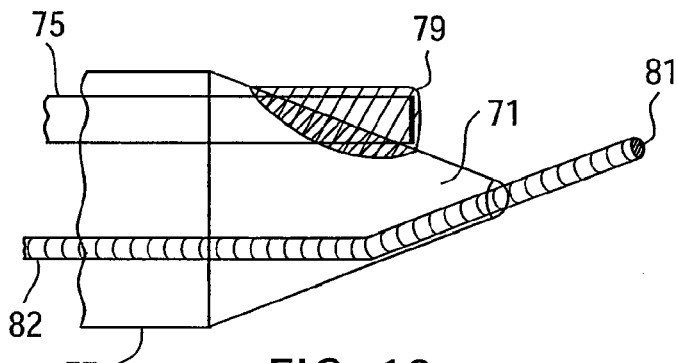
FIG. 10a is a partial side sectional view of another embodiment of a tissue dissecting tip according to the present invention.
Figure 10B:
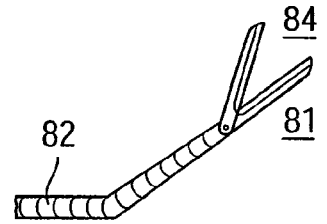
Figure 11A:
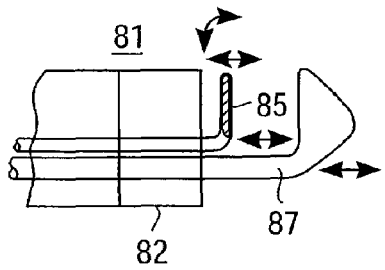
FIGS. 11a, 11b and 11c are, respectively, partial side pictorial views and an end view of end effectors in the embodiment of FIG. 8.
Figure 11B:
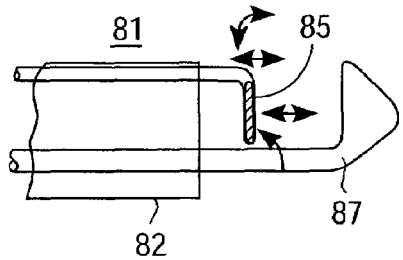
Figure 11C:
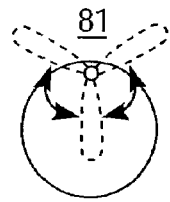

The end effector 81 may include another surgical instrument, as later described herein, such as a probe or tissue welder or tissue transector, or the like, that is supported on an elongated body 82 which is slidably extendable through another aperture 83 in the tip 71 positioned substantially at the apex thereof. The distal end of the end effector 81 may substantially conform to the shape of the walls of the tip 71 near the apex thereof to promote convenient utilization of the assembled cannula 77 for tissue dissection while configured as illustrated in FIG. 8. Of course, the aperture 83 through which the supporting body 82 extends and retracts does not have to be located at the apex of the tapered tip 71 but may instead be eccentrically oriented relative to the apex for extension through a portion of the tapered wall of the tip 71. Also, it should be noted that the supporting body 82 may be flexible, at least near the distal end thereof, or may be pre-formed with the distal end skewed from alignment with the portion of the body 82 disposed within the cannula 77, as illustrated in FIG. 10a. The end effector 81 may thereby be extended into and operated directly within the field of view of the endoscope 75 in the extended position. And, as illustrated in FIG. 10b, the end effector 81 may include operable jaws or scissor-like blades, as later described herein. Alternatively, the end effector 81 may include a transector, as illustrated in the partial side views of FIGS. 11a and 11b, to operate via translational movement of a tissue-welding end cutter element 85 relative to a distally-positioned anvil 87 that may include distal surfaces shaped substantially similarly to the wall of the tapered tip 71 near the apex thereof. Additionally, the element 85 may also rotate within the supporting body 82 to facilitate its use, for example as a tissue welder, within a range of angular orientations about the elongated axis of the cannula, as illustrated in FIG. 11c. This configuration of end effector 81 is thus capable of welding and cutting tissue disposed between the element 85 and the adjacent proximal surface of the anvil 87. The distal surface of the anvil 87 substantially conforms to the shape of the tapered walls of the tip 71 near the apex thereof.

Figure 12:
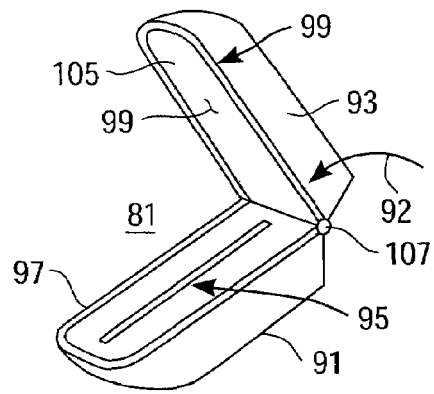
FIG. 12 is a partial perspective view of an end effector for the embodiment of FIG. 8.

Referring now to the partial perspective view of FIG. 12, there is shown an embodiment of an end effector 81 according to the present invention including a pair of jaw-like members 91, 93 that are pivoted for relative movement 92 between an open configuration, as illustrated, for receiving a tissue structure therebetween, and a closed configuration for clamping and treating a tissue structure between the closed members. In the illustrated embodiment, one of the members 91 includes a heater element 95 such as a resistive electrical conductor centrally disposed on a surface of the member that is adjacent the other member 93. In addition, another heater element 97, for example, a resistive electrical conductor, is disposed substantially about the periphery of the member 91 thereby to form peripheral and central heating zones on the tissue-engaging surface of the member 91. Similarly, a heater element 99 may also be disposed about the periphery of the mating surface of member 93 to contribute to heating of a vessel or other tissue structure in the peripheral zone. The members 91, 93 may be formed of ceramic or other electrically-insulating material that is capable of withstanding the elevated temperatures involved in operation of the end effector 81 without deterioration. And, the tissue-engaging surface of member 93 within the periphery thereof may be cushioned with a layer 105 of resilient material such as silicone rubber to apply resilient force against confined tissue for retaining the tissue in place and for aiding in thermally welding and severing the confined tissue. The members 91, 93 are supported on the body 82 and are linked to a proximal actuator in conventional manner (not shown) to undergo relative scissor-like movement about lateral pivot axis 107.

Figure 13:
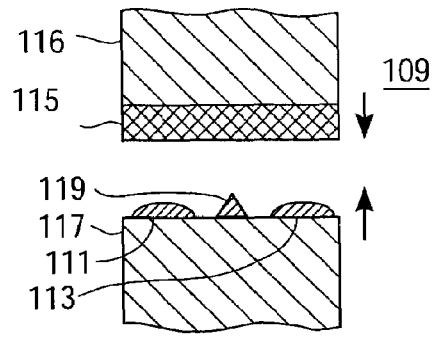
FIG. 13 is a partial end sectional view of an embodiment of an end effector in the embodiment of FIG. 8.

Referring now to the partial sectional end view of FIG. 13, there is shown an embodiment of end effector 109 similar to the embodiment of FIG. 12 including electrical conductors 111, 113 disposed near the periphery of at least one tissue-engaging surface of the relatively-movable members 116, 117, and including a centrally-disposed conductor 119 to form central and peripheral heating zones on the tissue-engaging surface of member 117. Additionally, the adjacent tissue-engaging surface of member 116 may include a resilient layer 115, and the centrally-disposed conductor 119 may be raised and blade-shaped to facilitate transection of tissue disposed between the members 116, 117. The electrical conductors 111, 113, 119 are resistive heaters that weld the tissue by applying heat. Additionally, resistive heaters may be disposed in complimentary pattern on the mating surface of member 116.

Figure 14A:
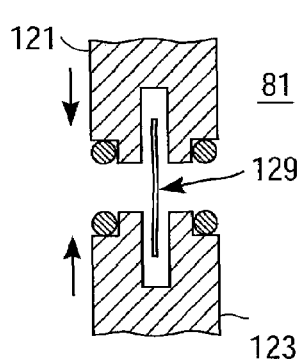
FIGS. 14a and 14b are partial end sectional views of end effectors for the embodiment of FIG. 8.
Figure 14B:
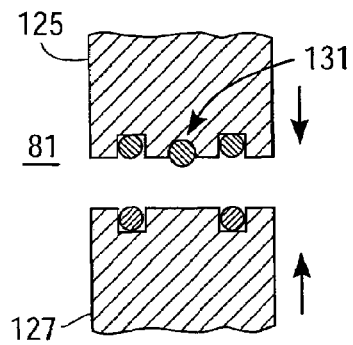

Referring now to the partial sectional end views of other embodiments of the end effector 81 of the present invention as illustrated in FIGS. 14a, and 14b, the relatively-movable mating members 121, 123, and 125, 127 each include electrical conductors disposed at or near the periphery of both members within grooves or recesses in the mating tissue-engaging surfaces. These electrical conductors serve as heaters and are recessed within the respective meeting surfaces. Additionally, each of these embodiments of end effectors 81 according to the present invention include a tissue transactor centrally disposed between the peripheral electrodes. As shown in FIG. 14a, blade 129 may selectively translate through confined tissue, and a heater element 131 as shown in FIG. 14b may selectively transect confined tissue when energized. The mating adjacent surfaces of these end effectors 81 include regions or plateaus adjacent the peripheral conductors to promote exertion of compressing force on confined tissue in order to enhance tissue sealing, or welding, of a blood vessel to inhibit bleeding as the vessel is transected.

Figure 14C:
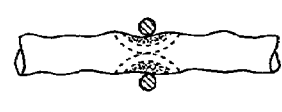
FIG. 14c is a partial side pictorial view showing thermal heating patterns attributable to heater elements disposed on opposite sides of a vessel.

Tissue structures such as blood vessels may be sealed using elevated temperature, under compressive force, applied for a selected time. Thus, compressive force applied to such tissue structures reduces the temperature and time required to seal the vessel. Accordingly, the adjacent mating surfaces of the end effectors 81 particularly adjacent the peripheral conductors are configured to exert compressive force on confined tissue (i.e., blood vessel) sufficient to accelerate sealing of the blood vessel on opposite sides of a location thereon at which the vessel is transected. And, as illustrated in the pictorial view of FIG. 14c, heating of a vessel from both sides, for sealing or transection, is beneficial to reduce the required heating time.

Figure 15A:
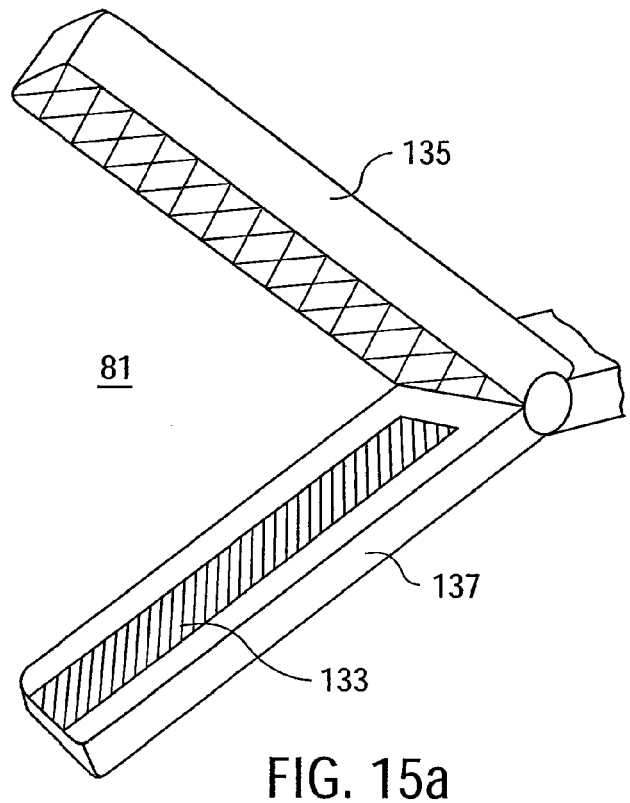
FIG. 15a is a partial perspective pictorial view of an end effector for the embodiment of FIG. 8.
Figure 15B:
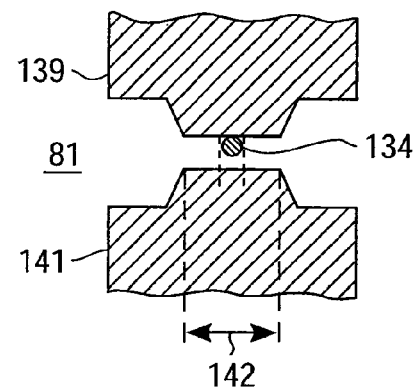
FIG. 15b is a partial end sectional view of another embodiment of an end effector for the embodiment of FIG. 8.

Referring now to FIGS. 15a and 15b, there are shown, respectively, partial perspective and end sectional views of other embodiments of end effectors 81 according to the present invention. Specifically, these embodiments include a single, central conductor 133, 134 disposed on one of the relatively-movable members 135, 137, 139, 141 to serve as a heater element for transecting a tissue structure such as a blood vessel, and to seal the vessel on opposite sides of the central conductor in response to the applied compressive force and lower temperature spaced away from the central conductor. A knurled or textured surface on a mating face of an adjacent member, as illustrated in FIG. 15a, aids in gripping the vessel as compressive force and cauterizing heat are applied to the vessel. This configuration holds the vessel in contact with the heater element despite lateral forces caused by heat-induced tissue shrinkage. Alternatively, in the embodiment illustrated in FIG. 15b, peripheral portions of the members 139, 141 are relieved or recessed to concentrate the compressive force within the region 142 immediately adjacent the central conductor or heater element 134. The recessed periphery concentrates the clamping force only where the tissue welding and transection occurs. Compressing tissue beyond this region can cause tissue to be undesirably pressed onto the sides of the hot wire causing the tissue to stick to the hot wire as the wire cools. Tissue in tension will fall away from the hot wire upon transection when the wire is hot. With the tissue not laterally compressed onto the wire, the tissue has less propensity to stick to the hot wire.

Figure 16:
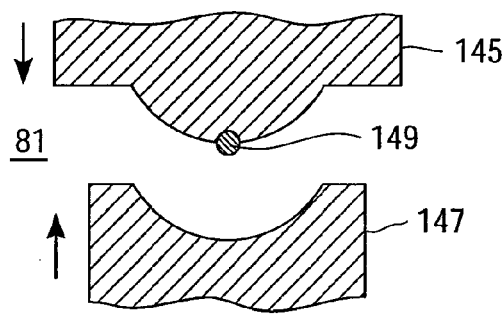
FIG. 16 is a partial end sectional view of another embodiment of an end effector for the embodiment of FIG. 8.

Referring now to FIG. 16 there is shown a partial end sectional view of another embodiment according to the present invention of an end effector 81 for welding and transecting a tissue structure such as a blood vessel. In this embodiment, mating relatively-movable members 145, 147 include curved mating faces that promote stretching of a tissue structure such as a blood vessel disposed laterally between the members 145, 147 as the central conductor or heater element 149 is pressed into a vessel. The curved contour of the mating faces tends to increase the length of a portion of a vessel that is confined between the members 145, 147 and thereby stretch and thin the vessel for more effective sealing thereof in response to heat and pressure applied thereto by the end effector 81.

Figure 17:
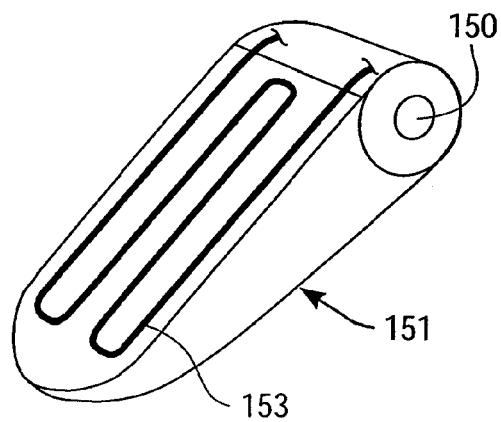
FIG. 17 is a partial perspective view of one of a pair of mating members of an end effector for cauterizing a tissue structure.

Referring now to FIG. 17, there is shown a perspective view of one 151 of a pair of mating members of an end effector 81 that may be pivoted together for rotation about a lateral pivot axis 150 to permit relative movement therebetween for confining a tissue structure in contact with a heater element 153. In this embodiment of an end effector 81 the heater element 153, which may be a resistive conductor or other heater structure is disposed in a serpentine pattern on the tissue-engaging surface for selectively heating confined tissue in peripheral and central regions of the surface. In this way, temperature profiling across the width of the surface (i.e., in substantial alignment with a blood vessel confined thereon), as illustrated in FIG. 21c or 23c, is achieved by spacing peripheral convolutes away from a central loop of closely-spaced conductors. This concentrates heating in such central region sufficient for transecting a confined vessel while promoting adequate heating in peripheral regions sufficient to weld or seal the vessel tissue.

Figure 18:
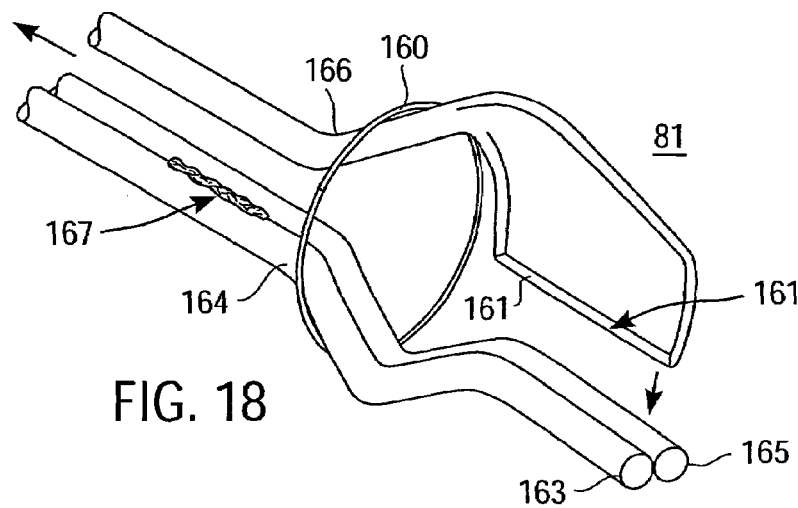
FIG. 18 is a partial perspective view of another embodiment of an end effector in accordance with the present invention.
Figures 19A, 19B, 19C:
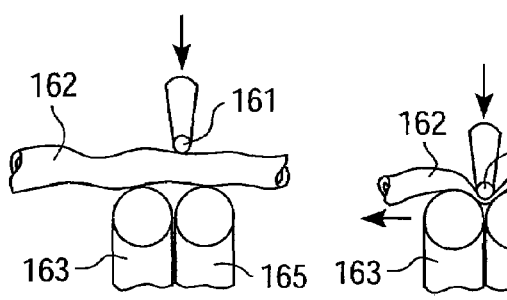
FIGS. 19a, 19b, and 19c are partial end views of operational configurations of the embodiment of FIG. 18.

Referring now to the perspective view of FIG. 18, there is shown an embodiment of the present invention in which a heater element 161 is disposed to move toward and between a pair of resilient rods 163, 165 that form a split anvil. The rods 163, 165 are attached together, for example, by a weld 167 at a location proximal the distal ends of the rods 163, 165 to facilitate resilient parting of the rods during transection of tissue such as a blood vessel. The FIGS. 19a, b, c are partial end views showing a sequence of operational configurations of the embodiment of FIG. 18 during tissue transection. As illustrated in FIG. 19c, pressing the heater element 161 down into and between the rods 163, 165 promotes efficient transection of a vessel 162 by combined effects of applied heat and pressure, and shearing passage through the vessel, and pulling movement of the rods 163, 165 to separate the severed portions of the vessel 162. In addition, lateral, spring biased movements of the anvil rods 163, 163 wipe coagulum from heat element 161. Reconfiguration of the end effector 81 that is structured as illustrated in FIG. 18 between open and closed configurations may be manually controlled, for example, by relatively translating the assembly proximally and distally through a confining ring 160 that engages ramped camming surfaces 164, 166. Such confining ring 160 may comprise the aperture 83 near the apex of the tip 71, as illustrated in FIG. 9, and the ends of the rods 163, 165, together with the distal end of the blade 161, may be shaped to conform substantially to the shape of the exterior walls of tissue-dissecting tip 71 near the apex thereof.

Figure 20A:
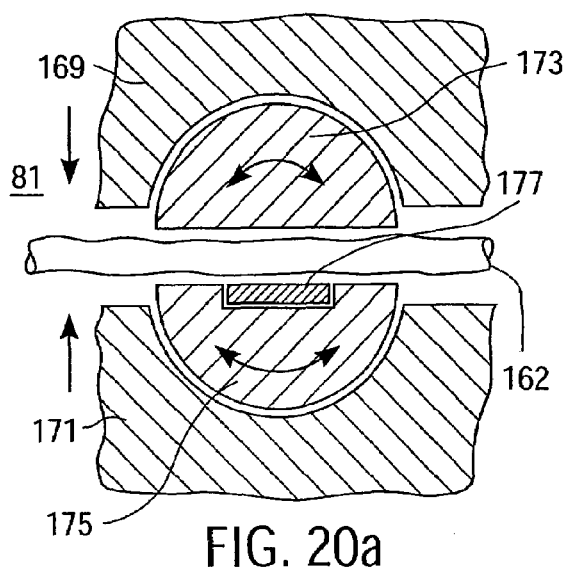
FIG. 20a is a partial end sectional view of another end effector for the embodiment of FIG. 8.

Referring now to FIG. 20a, there is shown a partial end sectional view of another embodiment of the present invention in which the end effector 81 includes a pair of mating members 169, 171 that are mounted for relative movement together, and that are each disposed to support a rotatable segment 173, 175 within a mating recess in the adjacent surfaces. In this configuration, the segments 173, 175 may rotate axially to orient the mating surfaces essentially parallel or otherwise aligned to apply compressive force and surface pressure substantially uniformly to a confined portion of vessel 162 for reliable sealing and transection of the vessel 162. One or more heater elements 177 of the various types previously described herein may be supported at central or peripheral locations on the mating surfaces. For example, a pair of heater elements may be disposed on the mating surfaces near the maximum diameters thereof.

Figure 20B:
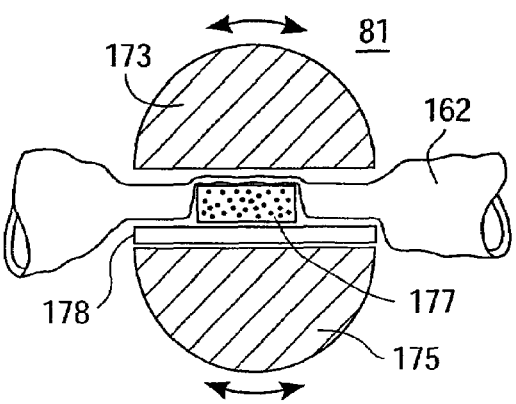

Referring now to FIG. 20b, there is shown a partial end sectional view of an end effector 81 in which rotatable segments 173, 175 of a tissue-clamping structure are mounted in a manner similar to the structure of FIG. 20a for exerting substantially uniform compressive force on a tissue structure such as vessel 162 across the length thereof disposed between the segments 173, 175. One such segment 175 supports a substantially flat heater element 177 mounted on a flexible pad or insulating layer 178 to protrude above the tissue-contacting surface thereof. The broad, flat heater element 177 in this configuration distributes compressive force over wider heater area than is possible with a heater wire, and this promotes more even heating of contacted tissue. In addition, heat transfer tends to continue as tissue desiccates and chars and shrinks away from the heater due to heat transfer from the lateral surfaces of the heater 177. Thus, charred tissue compressed within the central region in contact with the heater element 177 severs and recedes while tissue adjacent the lateral sides of the heater element 177 is less compressed and continues to be heated adequately from the lateral surfaces thereof to form reliable tissue welds. The flexible pad 178 aids in distributing the tissue-compressing force exerted on tissue being charred in contact with heater element 177, and contributes adequate compressive force to adjacent tissue being welded within the lateral or peripheral zones about the heater element 177.

Referring now to FIG. 21a, there is shown a pictorial end sectional view of an end effector 81 showing representative heater elements 181, 183, 185 disposed in at least one of the mating surfaces of the relatively movable segments 187, 189. The outermost heater elements 181, 185 are disposed near peripheral edges of the segments and are spaced away from the central heater element 183 to provide a temperature profile along a confined length of vessel 162 as illustrated, for example, in the graph of FIG. 21c. Specifically, a central region of the confined length of a vessel 162 may be heated by the central element 183 to an elevated temperature 191 sufficient to transect the vessel, while adjacent regions of the confined vessel 162 are heated to lower temperatures 192, 193 sufficient to seal the vessel with reliable welds of the vessel tissue. As illustrated in the schematic circuit diagram of FIG. 21b, the heater elements 181, 183, 185 may include resistive electrical conductors of various resistance values determined by the temperature requirement in the region to be heated, and supplied by a common source of electrical signal. Of course, other circuitry, and other heating schemes as previously described herein, may be used to heat and monitor individual elements 181, 183, 185 and the associated regions they occupy, for optimum temperature profiling along a confined length of a vessel 162 captivated between members 187, 189.

In each of the embodiments described herein that include one or more electrical conductors for forming heater elements, the conductors of the heater elements may include high-resistance wires or deposited layers of conductive material on ceramic or other temperature-tolerant insulative materials to dissipate power and produce heat that is transferred to contacted tissue. Such high resistance conductors may exhibit positive temperature coefficients of resistance and cooperate with supporting thermal mass or external controllers to maintain substantially uniform temperatures in the regions being heated. Alternatively, such high resistance conductors may exhibit negative temperature coefficients of resistance to dissipate increased power at reduced operating temperatures in order to provide a measure of self regulation of temperature as the heater elements are cooled in contact with tissue.

Referring now to the end sectional view of FIG. 22, an elongated body 82 in an embodiment according to the present invention for supporting an end effector 81, as illustrated in FIGS. 8 and 9, may include an outer tubular member 201 of substantially rigid construction for operation as illustrated in FIGS. 8 and 9. Alternatively, the elongated body 82 may be flexible for operation as shown in FIG. 10a. An inner tubular member 203 may be correspondingly rigid or flexible for slidable movement within the outer tubular member 201 for transferring actuating motion between proximal and distal ends of the cannula. Each of the inner tubular member 203 and outer tubular member 201 may be formed of bioinert, electrically-insulative polymer material or include a layer of insulation on electrically-conductive material. The inner tubular member 203 supports two or more electrical conductors 205, 207 that are electrically isolated from each other and that, in one embodiment, are formed as deposited layers of conductive material. These conductors 205, 207 are connected at the distal end of the body 82 to heater elements of the end effector 81, and are connected near the proximal end of the body 82 to a suitable supply of electrical signal (not shown) for selectively energizing the heater elements. An endoscope 209 is slidably supported within the bore of the inner tubular member 203 which is slidable or rotatable within the bore of the outer tubular member 201 to facilitate mechanical coupling and remote manual control of movable elements of an end effector 81, for example, as illustrated in FIG. 11a.

In operation of embodiments of the present invention, it is desirable to elevate the temperature of tissue either to weld the tissue, or to weld and transect the tissue. Thus, as illustrated in the graph of FIG. 23a, a single heater element may dissipate power to elevate the temperature thereof along an ideal temperature profile with time, as illustrated. To char and sever tissue, the temperature in the central region may elevate to about 300°-400° C., while the temperature in peripheral zones spaced less than one millimeter away from the heater element may diminish to about 100° C. or less as an ideal temperature for coagulating and sealing tissue as a result of denaturation of the tissue proteins. As illustrated in the graph of FIG. 23b, the tissue temperature 215 for welding and sealing a vessel tissue structure may be achieved over time and be held at substantially the desired temperature under compressive force for a period of time that varies as a function of the thickness of tissue being welded, but typically for only a few seconds. Such temperature profile avoids or at least delays loss of electrical and thermal conductivity as the tissue desiccates at the elevated temperatures associated with welding and sealing of the tissue structure. As illustrated in the graph of FIG. 23c, the temperature profile as a function of the location along a tissue-contacting surface of an end effector 81 may peak adjacent a central transecting heater element at a temperature, as described above, suitable for transecting tissue, and taper with distance from such heater element to lower temperatures suitable for welding and sealing a tissue structure at locations spaced away from the central heater element. Optionally, peripheral heater elements may be positioned as previously described herein to elevate the temperature profile in the peripheral regions, for example, as illustrated in the graph of FIG. 21c.

Referring now to the partial perspective view of FIG. 24, there is shown another embodiment of the present invention including a manipulatable probe 221 mounted near a tapered tissue-dissecting tip 223. The probe 221 is hinged and pivoted about mounting element 225 for lateral movement between open (as shown) and closed configurations, as well as for side-to-side movements relative to a raised segment 227 of the tapered wall of tip 223. In this embodiment, the tissue-dissecting tip 223 is mounted at the distal end of an endoscopic cannula 220 and is transparent to facilitate visualization therethrough of tissue being bluntly dissected by the tip 223 along the course of a vessel such as a saphenous vein that is to be harvested from its location in a patient's body. The raised segment 227 extends along the wall of the tip 223 in substantial axial alignment with the endoscopic cannula 220 and tip 223. The mounting element 225 near the distal end of endoscopic cannula 220 supports the probe 221 in a position of close proximity to the raised segment 227 in the 'closed' configuration of the instrument that facilitates blunt tissue dissection without significant impediments to its smooth passage through tissue. One or more control rods 228, 229 supported on the endoscopic cannula and coupled to the mounting element 225 extend to manual actuators near the proximal end of the endoscopic cannula 220 to provide remote manual control of the movement of probe 221 relative to the raised segment 227. Thus, as illustrated in the partial end sectional views of FIGS. 25 a, b, c, the probe 221 may be manipulated from side to side relative to the raised segment 227 as well as laterally up and down between open and closed configurations. One or both of the probe 221 and raised segment 227 may support a resistive conductor or other heater element 230 to generate heat for transfer to a tissue structure such as a blood vessel 162 that is compressed between the probe 221 and raised segment 227. Thus, the probe 221 may be positioned closely adjacent the raised segment 227 in the closed configuration of the instrument during tissue dissection by advancement of the tapered tip 223 through tissue, and may then be re-configured in situ to the open configuration, as illustrated in FIG. 24, to capture a side branch vessel 162 between probe 221 and raised segment 227, as illustrated in FIG. 25a. The pivotal attachment of the probe 221 by mounting element 225 promotes convenient capture of a blood vessel on either side of the tip 223 for compression of the vessel between the raised segment 227 and the probe 221 as again re-positioned in the closed configuration. A vessel or other tissue structure thus captured and compressed between the raised segment 227 and probe 221 is then tissue welded and severed by application of heat thereto from the heater element 230 such as a hot resistance wire supported by one or both of the raised segment 227 and probe 221.

Therefore, the tissue-dissecting tip and tissue welder of the present invention facilitates efficient dissection of side-branch vessel tissue along a blood vessel such as a saphenous vein or radial artery, and also facilitates convenient compression and hemostatic severing of such side branch vessels during vessel-harvesting procedures. Various end effectors selectively configure the tip for tissue dissecting and for hemostatic tissue welding and severing of the side-branch vessels from the target vessel being harvested.

What is claimed is:
1. A surgical instrument comprising:
an elongated body extending between distal and proximal ends thereof;
a tissue-dissecting tip disposed at the distal end of the body and including a conical exterior wall that converges distally for dissecting tissue in contact therewith;
an arm mounted for movement toward and away from the exterior wall of the tip between an open configuration in which the arm is skewed relative to the exterior wall of the tip and a closed configuration in which the arm is substantially flush within the exterior wall for confining tissue between the arm and the exterior wall to apply compressive force to the confined tissue in response to movement of the arm from the open toward the closed configurations;
a tissue welder supported with respect to the exterior wall in said closed configuration of substantial unobtrusive position and for exposure in said open configuration to confine tissue disposed between the arm and the exterior wall; and controls disposed near the proximal end of the body and communicating with the arm and tissue welder for selectively moving the arm between configurations for confining tissue between the arm and exterior wall, and for energizing the tissue welder in response to manual actuation of the controls during position of the arm to apply compressive force to tissue confined between the arm and the exterior wall.

2. The surgical instrument according to claim 1 in which the tissue welder is supported on the arm to contact tissue confined against the exterior wall by the arm.

3. The surgical instrument according to claim 1 including a recess in the exterior wall of the tip, and in which the tissue welder is mounted in the recess in the exterior wall of the tip.

4. The surgical instrument according to claim 1 in which the tip includes a recess in the exterior wall thereof substantially in alignment with an elongated axis of the body; and said arm is mounted for movement about an axis transverse to the elongated body to retract into said recess in the closed configuration.

5. The surgical instrument according to claim 4 in which the tissue welder is mounted within the recess for concealment in the closed configuration and exposure in the open configuration of the arm.

6. The surgical instrument according to claim 1 in which the body includes a lumen extending between the distal and proximal ends thereof for slidably supporting an actuator therein, and further comprises:

a housing attached near the proximal end of the body; and a manual control mounted on the housing coupled to an actuator disposed within said lumen and communicating with the arm for selectively moving the arm between the closed and open configurations in response to manual actuation of the manual control.

7. The surgical instrument according to claim 6 in which the body supports a channel to the tissue welder for selectively controlling energy supplied thereto through the channel in response to manual actuation of the controls.

8. The surgical instrument according to claim 1 in which the tissue welder is responsive to energy received thereby to heat to tissue-welding temperature the tissue confined against the exterior wall by the arm.

9. A surgical instrument comprising:

an elongated body extending between distal and proximal ends thereof;

a tissue-dissecting transparent tip disposed at the distal end of the body and including exterior walls configured to dissect tissue in contact therewith, the tip substantially enclosing the distal end of the body that includes a lumen therein extending between the distal and proximal ends thereof for receiving an endoscope within the lumen in alignment with the transparent tip for providing endoscopic visualization therethrough of tissue dissection in contact with the exterior walls;

an arm mounted for movement relative to an exterior wall of the tip between a closed configuration and an open configuration in which the arm is skewed relative to the exterior wall of the tip;

a tissue welder supported with respect to the exterior walls in said closed configuration of substantial unobtrusive position and for exposure in said open configuration; and controls communicating with the arm and tissue welder for selectively moving the arm between configurations and energizing the tissue welder in response to manual actuation of the controls.

* * * * *